United States Patent
Ali et al.

(10) Patent No.: US 9,937,292 B2
(45) Date of Patent: Apr. 10, 2018

(54) SYSTEMS FOR FILLING A FLUID INFUSION DEVICE RESERVOIR

(71) Applicant: MEDTRONIC MINIMED, INC., Northridge, CA (US)

(72) Inventors: Sherif M. Ali, Porter Ranch, CA (US); Thomas P. Miller, Porter Ranch, CA (US); Vaughn S. Sakae, Arcadia, CA (US); Edgardo C. Halili, Santa Clarita, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 501 days.

(21) Appl. No.: 14/564,901

(22) Filed: Dec. 9, 2014

(65) Prior Publication Data
US 2016/0158104 A1    Jun. 9, 2016

(51) Int. Cl.
*A61M 5/178*    (2006.01)
*A61J 1/20*    (2006.01)

(52) U.S. Cl.
CPC .......... *A61M 5/1782* (2013.01); *A61J 1/2096* (2013.01); *A61J 1/201* (2015.05); *A61J 1/2037* (2015.05); *A61J 1/2048* (2015.05); *A61J 1/2058* (2015.05); *A61J 1/2079* (2015.05)

(58) Field of Classification Search
CPC ........ A61J 1/201; A61J 1/2096; A61J 1/2048; A61J 1/2058; A61J 1/2037; A61M 39/223; A61M 5/162; A61M 5/1782
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Bradley Osinski
(74) *Attorney, Agent, or Firm* — Lorenz & Kopf, LLP (57) ABSTRACT

A transfer device for filing a fluid reservoir of a fluid infusion device with a fluid is provided. The transfer device comprises a first end to couple to a source of the fluid, and a second end to couple to a pressurizing device. The transfer device also comprises a body interconnecting the first end and the second end, and having an end to couple to the fluid reservoir. The body defining at least one fluid flow path between the source of the fluid, the pressurizing device and the fluid reservoir to enable the filling of the fluid reservoir with the fluid.

16 Claims, 5 Drawing Sheets

(56) References Cited

U.S. PATENT DOCUMENTS

| | | | |
|---|---|---|---|
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 4,950,254 A * | 8/1990 | Andersen | A61J 15/0026 604/213 |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,485,408 A | 1/1996 | Blomquist | |
| 5,505,709 A | 4/1996 | Funderburk et al. | |
| 5,497,772 A | 5/1996 | Schulman et al. | |
| 5,543,326 A | 8/1996 | Heller et al. | |
| 5,562,616 A * | 10/1996 | Haber | A61J 1/2089 604/191 |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Illiff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,259,937 B1 | 7/2001 | Schulman et al. | |
| 6,329,161 B1 | 12/2001 | Heller et al. | |
| 6,364,865 B1 * | 4/2002 | Lavi | A61J 1/2089 604/411 |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,474,375 B2 * | 11/2002 | Spero | A61J 1/2089 141/329 |
| 6,484,045 B1 | 11/2002 | Holker et al. | |
| 6,484,046 B1 | 11/2002 | Say et al. | |
| 6,485,465 B2 | 11/2002 | Moberg et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |

(56) References Cited

U.S. PATENT DOCUMENTS

| | | |
|---|---|---|
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 7,828,764 B2 | 11/2010 | Moberg et al. |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2009/0299290 A1 | 12/2009 | Moberg |
| 2010/0305548 A1* | 12/2010 | Kraushaar ............ A61J 1/2096 604/518 |
| 2014/0207065 A1 | 7/2014 | Yavorsky |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Inulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.

(56) References Cited

OTHER PUBLICATIONS (MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . , pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal-Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jonsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethyiphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

(56) References Cited

OTHER PUBLICATIONS

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of ansimplantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

SYSTEMS FOR FILLING A FLUID INFUSION DEVICE RESERVOIR

TECHNICAL FIELD

Embodiments of the subject matter described herein relate generally to fluid infusion devices for delivering a medication fluid to the body of a user. More particularly, embodiments of the subject matter relate to systems for filling a fluid reservoir of a fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a suitable hollow tubing. In many instances, the fluid reservoir requires filling by the patient prior to use in the external fluid infusion device. This process can be tedious and time consuming.

Accordingly, it is desirable to provide improved systems for filling a fluid reservoir of a fluid infusion device. Furthermore, other desirable features and characteristics will become apparent from the subsequent detailed description and the appended claims, taken in conjunction with the accompanying drawings and the foregoing technical field and background.

BRIEF SUMMARY

According to various embodiments, a transfer device for filling a fluid reservoir of a fluid infusion device with a fluid is provided. The transfer device comprises a first end to couple to a source of the fluid, and a second end to couple to a pressurizing device. The transfer device also comprises a body interconnecting the first end and the second end, and having an end to couple to the fluid reservoir. The body defining at least one fluid flow path between the source of the fluid, the pressurizing device and the fluid reservoir to enable the filling of the fluid reservoir with the fluid.

Also provided is a system for filling a fluid reservoir of a fluid infusion device with a fluid. The system comprises the fluid reservoir including a port for receipt of the fluid, and a transfer device having a body. The body has an end coupleable to the port of the fluid reservoir, a first end to couple to a source of the fluid and a second end to couple to a pressurizing device. The body defines at least one fluid flow path between the source of the fluid, the pressurizing device and the fluid reservoir to enable the filling of the fluid reservoir with the fluid.

According to various embodiments, a system for filling a fluid reservoir of a fluid infusion device with a fluid is provided. The system comprises a source of pressure, and the fluid reservoir including a port for receipt of the fluid. The system also comprises a transfer device including a body having a first branch, a second branch and a third branch. The first branch to couple to a source of the fluid, the second branch coupleable to the source of pressure and the third branch coupleable to the fluid reservoir. A valve is disposed in the first branch, and the valve is responsive to the source of pressure to permit the fluid to flow into the body. The body defining at least one fluid flow path between the source of the fluid, the pressurizing device and the fluid reservoir to enable the filling of the fluid reservoir with the fluid.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

Figure 1:
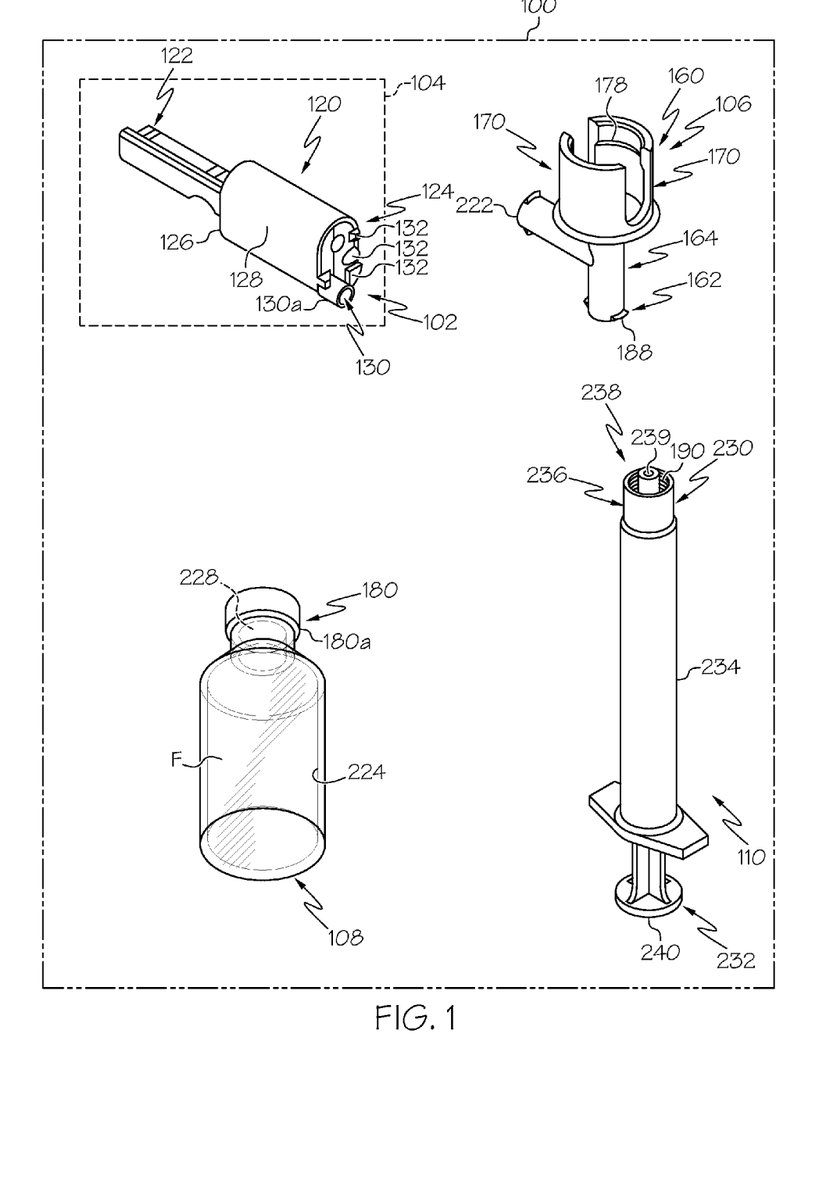
FIG. 1 is a perspective view of an exemplary embodiment of a system for filling a fluid reservoir system of a fluid infusion device according to various teachings of the present disclosure.
Figure 2:
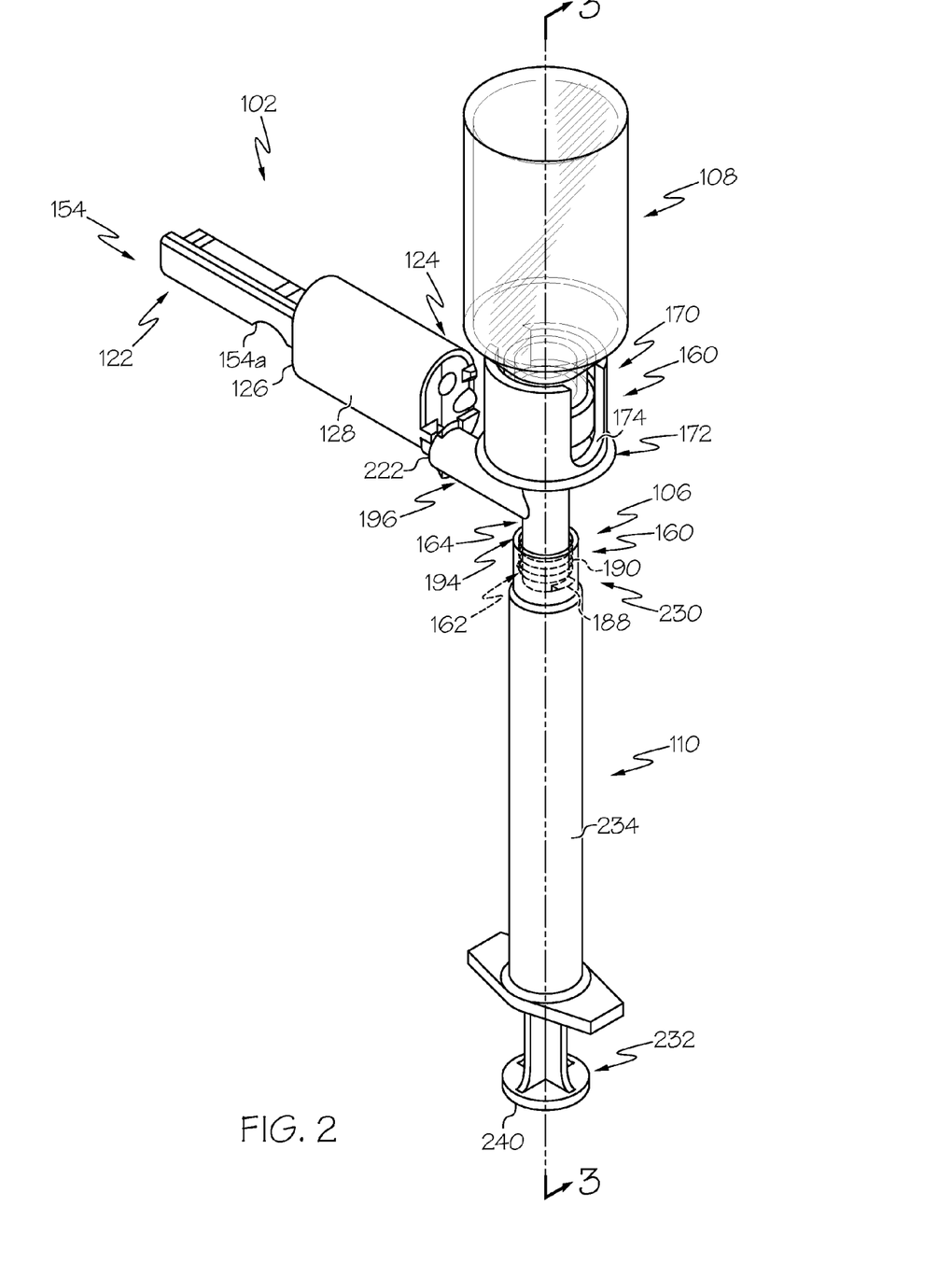
FIG. 2 is perspective view of the system of FIG. 1 assembled to fill the fluid reservoir of the fluid infusion device.

FIG. 1 is a perspective view of an exemplary embodiment of a system 100 for filling a fluid reservoir 102 of a fluid infusion device 104. The system 100 includes the fluid reservoir 102 of the fluid infusion device 104, a transfer device 106, a vial 108 and a pressurizing device 110. One or more components of the system 100 can be packaged together in suitable packaging for use by a consumer. With reference to FIG. 2, the system 100 enables the consumer to fill the fluid reservoir 102 of the fluid infusion device 104 with all or a portion of the contents of the vial 108, as will be discussed in greater detail herein.

With reference to FIG. 1, as the fluid infusion device 104 comprises any suitable fluid infusion device known in the art, the fluid infusion device 104 will not be discussed in great detail herein. For example, the fluid infusion device 104 can comprise an insulin infusion device, such as the MiniMed Paradigm® REAL-Time Revel™ Insulin Pump, offered for sale by Medtronic MiniMed, Inc. of Northridge, Calif. Briefly, the fluid infusion device 104 is designed to be carried or worn by the patient. The fluid infusion device 104 may leverage a number of conventional features, components, elements, and characteristics described in U.S. Pat. Nos. 6,485,465 and 7,621,893, the relevant content of which is incorporated by reference herein. In addition, the fluid infusion device 104 can comprise the fluid infusion device described in U.S. Publication No. 2014/0207065, which is incorporated by reference herein.

With continued reference to FIG. 1, the fluid reservoir 102 can be removably coupled to the fluid infusion device 104. In one example, the fluid reservoir 102 can comprise the fluid reservoir described in U.S. Publication No. 2014/0207065, which is incorporated by reference herein. It should be understood, however, that the fluid reservoir 102 can comprise any suitable fluid reservoir 102 that is capable of receiving and/or dispensing a fluid, and thus, the fluid reservoir 102 described and illustrated herein is merely exemplary.

As illustrated in FIG. 1, the fluid reservoir 102 includes a first or barrel portion 120 and a second portion or plunger guide 122. Generally, the barrel portion 120 includes a first end 124, a second end 126 and a reservoir 128 defined between the first end 124 and the second end 126.

The first end 124 cooperates with the fluid infusion device 104 to couple the fluid reservoir 102 to the fluid infusion device 104. In one example, the first end 124 of the barrel portion 120 includes a delivery port 130 and one or more alignment features 132. It should be noted that the use of three alignment features 132 is merely exemplary, as the barrel portion 120 could include any number of alignment features 132 to aid in coupling the fluid reservoir 102 to the fluid infusion device 104.

Figure 3:
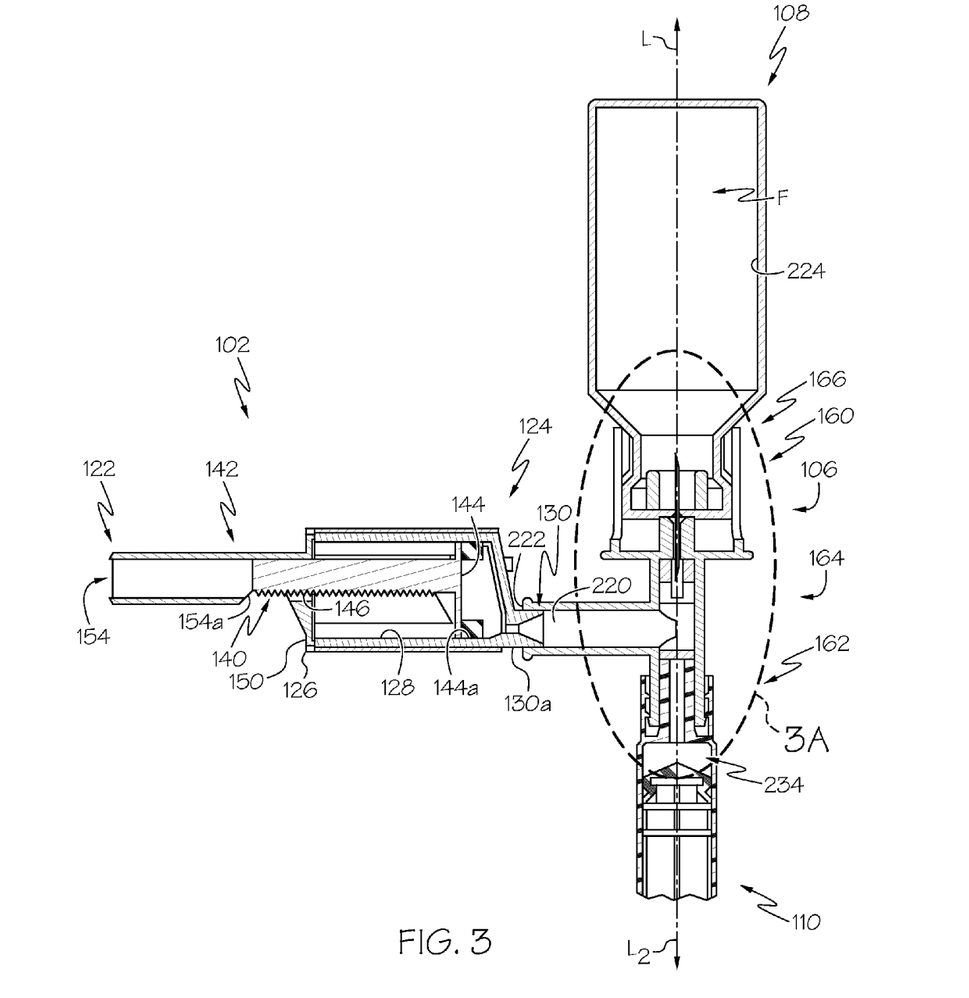
FIG. 3 is a cross-sectional view of the system of FIG. 2, taken along line 3-3 of FIG. 2.

The delivery port 130 establishes a fluid flow path into and from the reservoir 128. The delivery port 130 can be coupled to the transfer device 106 for filling the fluid reservoir 102 and can be coupled to a set connector for establishing a fluid flow path out of the fluid reservoir 102. The delivery port 130 can include a vented opening to accommodate filling of the fluid reservoir 102 by the patient, a doctor, a caregiver, or the like. In one example, the delivery port 130 is cylindrical, with a smooth exterior surface 130a, to mate with the transfer device 106 (FIG. 3). It should be noted, however, that the delivery port 130 can include one or more threads or other coupling devices known to one skilled in the art to facilitate coupling the transfer device 106 to the delivery port 130.

With reference to FIG. 3, the second end 126 of the fluid reservoir 102 is substantially circumferentially open, and cooperates with a portion of the plunger guide 122. The reservoir 128 is defined between the first end 124 and the second end 126. As will be discussed in greater detail below, the reservoir 128 is fillable with a fluid from the vial 108 using the transfer device 106. In this example, the reservoir 128 is fillable with insulin from the vial 108, but the reservoir 128 can be fillable any suitable liquid.

The plunger guide 122 is movable to dispense fluid from the reservoir 128. The plunger guide 122 includes a plunger 140 and a housing 142. The plunger 140 can move relative to the housing 142. Generally, the plunger 140 includes a platform 144 and a rack 146 coupled to the platform 144. The platform 144 includes at least one sealing element 144a, which is circumferentially disposed about a perimeter of the platform 144. The sealing element 144a prevents fluid from escaping from the second end 126 of the reservoir 128 when the plunger guide 122 is coupled to the second end 126.

The rack 146 is fixedly coupled to the platform 144 so that the advancement of the rack 146 moves the platform 144 within the reservoir 128. The rack 146 includes a plurality of teeth, which can meshingly engage a plurality of teeth on a pinion coupled to the fluid infusion device 104. When coupled to the fluid infusion device 104, the rack 146 can be driven by the pinion to advance the platform 144 within the reservoir 128 to dispense fluid out of the delivery port 130. The rack 146 is movable between a variety of positions to enable the filling of the reservoir 128 with fluid and to enable the dispensing of the fluid from the reservoir 128. As illustrated in FIG. 3, the rack 146 is positioned in a first, empty position as the reservoir 128 is filled. In a second, filled position, the rack 146 and the platform 144 are near the second end 126 of the barrel portion 120.

The housing 142 includes a base 150 and a rack receiving portion 152. The base 150 is sized and configured to be received within and coupled to the second end 126 of the barrel portion 120. The base 150 defines an opening, which slidably receives a portion of the rack 146 therethrough. The opening of the base 150 is in communication with the rack receiving portion 152.

The rack receiving portion 152 extends outwardly from the base 150. The rack receiving portion 152 includes a bore or cavity 154. In one example, the cavity 154 is sized to movably or slidably receive the rack 146, and is in communication with the opening of the base 150. The cavity 154 also includes a cutout portion 154a, which enables the rack 146 to engage the pinion.

Figure 3A:
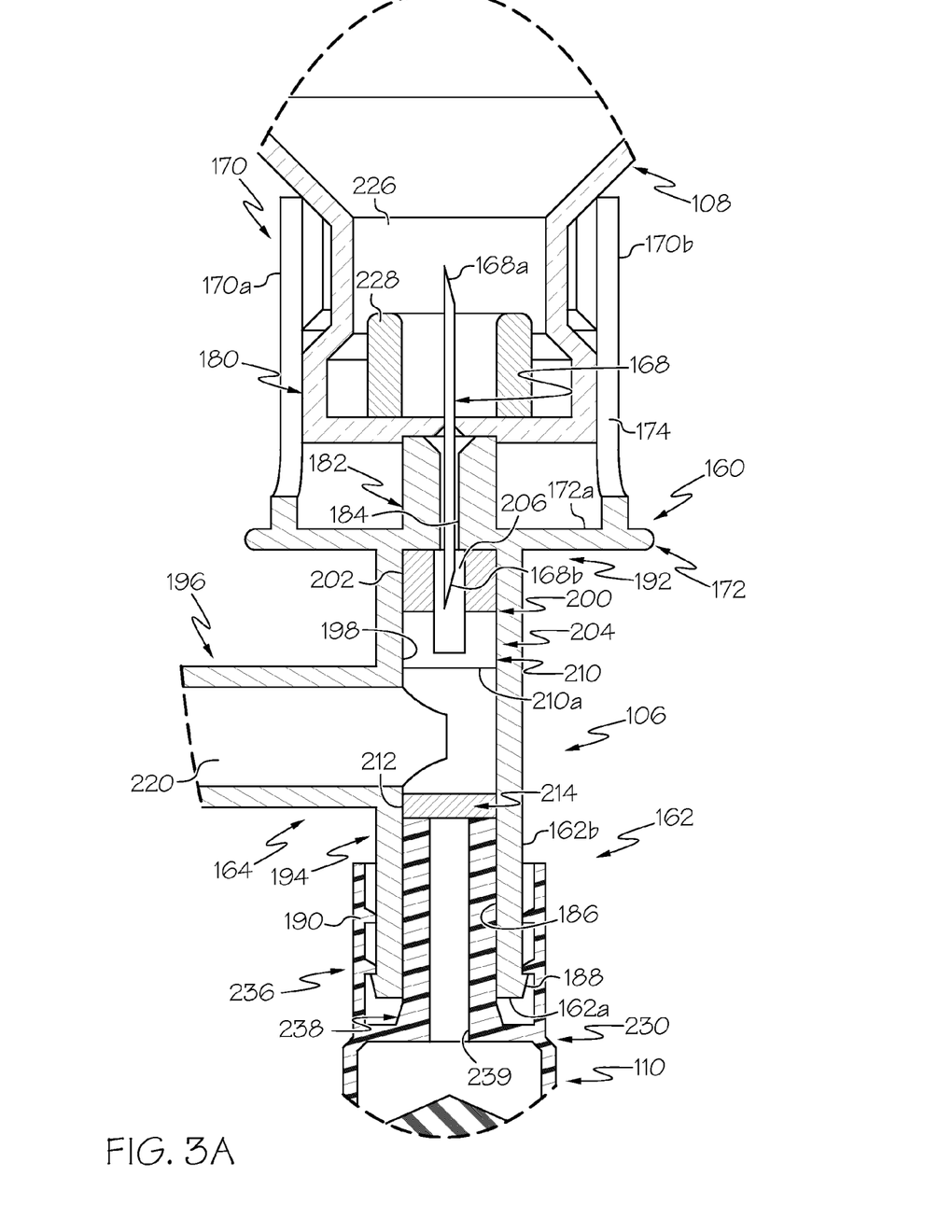
FIG. 3A is a detail cross-sectional view of a portion of the system of FIG. 3.
Figure 4:
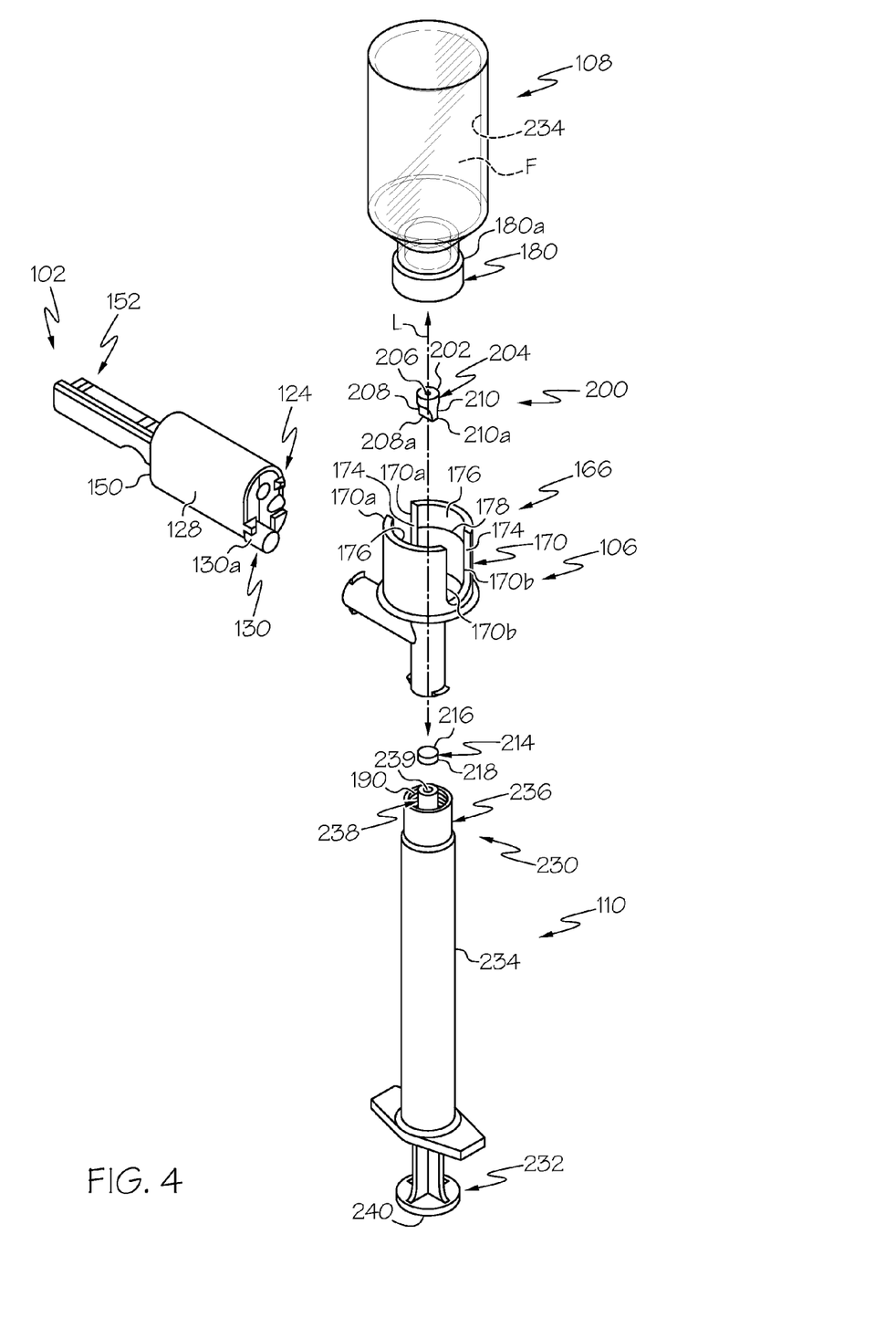
FIG. 4 is an exploded perspective view of the system of FIG. 1.

As illustrated in FIG. 2, the transfer device 106 can be coupled to the fluid reservoir 102, the vial 108 and the pressurizing device 110. The transfer device 106 can be composed of any suitable material, such as a biocompatible polymer. The transfer device 106 includes a first end 160 and a second end 162, which can be interconnected via a body 164. With reference to FIGS. 3, 3A and 4, the first end 160 includes a receiving portion 166 and a piercing member 168 (FIG. 3A). The receiving portion 166 receives a portion of the vial 108 to couple the vial 108 to the transfer device 106. With reference to FIG. 4, the receiving portion 166 is illustrated herein as substantially U-shaped, however, the receiving portion 166 can have any suitable shape to mate with a portion of the vial 108. In this example, the receiving portion 166 includes one or more projections 170, which coupled to and extend outwardly from a base 172.

With reference to FIG. 4, the projections 170 are spaced apart on the base 172 so as to define opposing apertures 174. The apertures 174 can enable a user to visually ensure the vial 108 is properly coupled to the receiving portion 166 and also enable the user to grip the vial 108 through the apertures 174. Generally, the projections 170 extend upwardly from the base 172 so as to extend parallel to a longitudinal axis L of the transfer device 106. The projections 170 are coupled to the base 172 such that the projections 170 are symmetrical with respect to the longitudinal axis L of the transfer device 106. Each of the projections 170 includes an interior surface 176 and a ledge 178. In one example, the interior surface 176 is concave to cooperate with an exterior surface of the vial 108. It should be noted that the interior surface 176 can have any desired surface shape to cooperate with the vial 108, and thus, the illustration herein is merely exemplary.

The ledge 178 is defined about the interior surface 176 and can extend along the interior surface 176 from a first end 170a of the projection 170 to a second end 170b of the projection 170. The ledge 178 cooperates with a portion of the vial 108 to secure the vial 108 within the receiving portion 166. For example, the ledge 178 cooperates with a flange 180 of the vial 108 to couple the vial 108 to the transfer device 106. In this regard, the ledge 178 can rest against an edge 180a of the flange 180 of the vial 108 to retain the vial 108 within the receiving portion 166. The ledge 178 can also be sized so as to extend outwardly from the interior surface 176 to cause a press-fit between the flange 180 of the vial 108 and the receiving portion 166. This can provide the user with tactile feedback that the vial 108 is coupled to the receiving portion 166.

With reference to FIG. 3A, the base 172 is substantially planar, and the projections 170 extend outwardly from a surface 172a of the base 172. Generally, the projections 170 extend outwardly from a perimeter of the base 172, however, the projections 170 can extend from the base 172 at any desired location based on a circumference or perimeter of the flange 180 of the vial 108. The base 172 also includes a central protrusion 182. The central protrusion 182 extends outwardly from the surface 172a of the base 172. The central protrusion 182 extends outwardly from the surface 172a for a distance that is different or less than a distance that the projections 170 extend from the base 172. The central protrusion 182 can be defined on the base 172 along a longitudinal axis L2 of the system 100. The central protrusion 182 includes a throughbore 184. The throughbore 184 is sized and shaped to receive the piercing member 168 therein, and thus, the central protrusion 182 can also serve to support or impart rigidity to the piercing member 168.

The piercing member 168 is received through the throughbore 184 of the base 172. The piercing member 168 can be coupled to the throughbore 184 through any suitable technique, such as press-fit, adhesive bonding, ultrasonic welding, etc. In one example, the piercing member 168 comprises a hollow needle or cannula to enable fluid to flow through the piercing member 168. The piercing member 168 has a piercing tip 168a to establish a fluid flow path out of the vial 108 and into the body 164 of the transfer device 106. The projections 170 of the receiving portion 166 generally extend outwardly from the base 172 for a distance greater than the piercing tip 168a to act as a guard for the piercing tip 168a. An end 168b of the piercing member 168 substantially opposite the piercing tip 168a is in fluid communication with the body 164.

The second end 162 of the transfer device 106 is substantially cylindrical to couple the second end 162 to the pressurizing device 110. It should be noted that the shape of the second end 162 described and illustrated herein is merely exemplary, as the second end 162 can have any desired shape to couple the pressurizing device 110 to the transfer device 106. In one example, the second end 162 defines a bore 186 and includes at least one coupling feature 188.

The bore 186 is defined through the second end 162 at a distalmost end 162a of the second end 162 to define a fluid flow path into the body 164. The bore 186 is substantially cylindrical and sized to receive a portion of the pressurizing device 110. It should be noted that the shape of the bore 186 is merely exemplary, as the bore 186 can have any desired shape.

The at least one coupling feature 188 is defined on an exterior surface 162b of the second end 162. The at least one coupling feature 188 cooperates with at least one coupling feature 190 of the pressurizing device 110 to couple the pressurizing device 110 to the transfer device 106. In one example, the at least one coupling feature 188 comprises one or more threads, which can include a Luer taper to define a female Luer-lock fitting and the at least one coupling feature 190 comprises one or more threads, which can include a Luer taper to define a male Luer-lock fitting. Thus, the pressurizing device 110 can be coupled to the second end 162 through a suitable Luer-lock connection. It should be noted that any suitable coupling features 188, 190 can be used to couple the transfer device 106 to the pressurizing device 110, such as a snap-fit, etc. and furthermore, the pressurizing device 110 can be integrally formed with the transfer device 106, if desired. Thus, the coupling features 188, 190 illustrated and described herein are merely exemplary.

With reference to FIG. 3, the body 164 of the transfer device 106 can fluidly interconnect or couple the fluid reservoir 102, the vial 108 and the pressurizing device 110 to each other. The body 164 can be substantially T-shaped, however, the body 164 can have any desired shape to fluidly interconnect or couple the fluid reservoir 102, the vial 108 and the pressurizing device 110 together. In this example, with reference to FIG. 3A, the body 164 includes a first branch 192, a second branch 194 and a third branch 196. The first branch 192, second branch 194 and third branch 196 can be coupled together to define one or more fluid flow paths through the body 164. The first branch 192 and the second branch 194 can extend along the longitudinal axis L2, and the third branch 196 can be substantially transverse to the longitudinal axis L2. In one example, the third branch 196 is substantially perpendicular to the longitudinal axis L2.

The first branch 192 is coupled to the first end 160. The first branch 192 is substantially cylindrical and is hollow, defining a passage 198. The first branch 192 also includes a valve 200, which is positioned within the passage 198 adjacent to the first end 160. The valve 200 is in communication with the piercing member 168 and receives the end 168b of the piercing member 168 to enable fluid communication between the vial 108 and the passage 198. In this regard, the valve 200 restricts the flow of fluid F from the vial 108 through the piercing member 168. The valve 200 is generally a one-way valve to allow the fluid F to exit the vial 108, while preventing the flow of fluid F back into the vial 108.

In one example, with reference to FIG. 4, the valve 200 is a duckbill valve having a first end 202, a second end 204 and a bore 206. The bore 206 is defined through the valve 200 from the first end 202 to the second end 204. The bore 206 receives and is coupled about the end 168b of the piercing member 168 to define a fluid flow path from the vial 108, through the piercing member 168 into the valve 200.

The first end 202 can be substantially cylindrical and sized to be received in the passage 198. In one example, the first end 202 can be press-fit into the passage 198 of the first branch 192, however, the first end 202 of the valve 200 can be coupled to the first branch 192 through any suitable technique, such as, ultrasonic welding, for example. The second end 204 is generally flattened, with a first member 208 and a second member 210. The first member 208 and the second member 210 are coupled to the first end 202 and are movable between a first position and a second position. In the first position, an end 208a of the first member 208 and an end 210a of the second member 210 are in contact with each other to effectively occlude or block the bore 206, thereby preventing fluid flow through the valve 200. In the second position, the end 208a of the first member 208 and the end 210a of the second member 210 are spaced apart from each other to effectively open the bore 206, thereby providing a fluid flow path through the valve 200.

Generally, as will be discussed further herein, the pressurizing device 110 can move the first member 208 and the second member 210 between the first position and the second position. In this regard, upon the application of a negative pressure to the transfer device 106, the first member 208 and the second member 210 move from the first position to the second position. Once the body 164 of the transfer device 106 returns to a positive pressure, the first member 208 and the second member 210 move from the second position to the first position. Stated another way, the application of a negative pressure to the transfer device 106 causes the second end 204 of the valve 200 to open, thereby allowing fluid to flow from the vial 108 into the passage 198 of the first branch 192 of the transfer device 106. The removal of the negative pressure causes the second end 204 of the valve 200 to close, thereby preventing fluid flow from the vial 108 into the passage 198 of the first branch 192.

With reference to FIG. 3A, the second branch 194 is coupled to the second end 162. The second branch 194 is substantially cylindrical and is hollow, defining a second passage 212. The second passage 212 receives a portion of the pressurizing device 110 and is in fluid communication with the pressurizing device 110. The second branch 194 also includes a filter 214. The filter 214 is coupled to the second branch 194. The filter 214 is positioned within the second passage 212 so as to be spaced apart from the second end 162 and adjacent to the third branch 196. Generally, the filter 214 is positioned within the second passage 212 so as to be adjacent to a portion of the pressurizing device 110 when the portion of the pressurizing device 110 is received in the second passage 212. The filter 214 is generally coupled to the second branch 194 through a suitable coupling technique, such as ultrasonic welding, adhesive bonding, etc., however, the filter 214 can also be press-fit into the second branch 194.

With reference to FIG. 4, the filter 214 can be substantially circular or cylindrical and sized to be received within the second branch 194. The filter 214 has a first side 216 and a second side 218. The first side 216 of the filter 214 faces the first branch 192 when the filter 214 is coupled to the second branch 194, and the second side 218 faces the second end 162. In one example, the filter 214 is a hydrophilic filter. Thus, the filter 214 enables air and fluid to flow into the pressurizing device 110 when a negative pressure is applied by the pressurizing device 110, and allows only fluid to flow back into the transfer device 106 when a positive pressure is applied by the pressurizing device 110.

With reference to FIG. 3A, the third branch 196 is substantially cylindrical and hollow, defining a third passage 220. The third passage 220 is in fluid communication with the passage 198 and the second passage 212. The third passage 220 extends through the third branch 196 from the first branch 192 and the second branch 194 to an end 222 (FIG. 3). The end 222 has a substantially open perimeter or circumference for receipt of the delivery port 130 of the fluid reservoir 102. Generally the circumference of the end 222 can be sized to be received over the exterior surface 130a of the delivery port 130 to enable the delivery port 130 to be press-fit into the third branch 196. It should be noted that the end 222 and the exterior surface 130a of the delivery port 130 can have any desired cooperating features to enable the fluid reservoir 102 to be coupled to the transfer device 106, such as mating threads, and thus, the use of the press-fit as described and illustrated herein is merely exemplary.

The vial 108 can comprise any suitable vial for storing a fluid. In one example, with reference to FIG. 3, the vial 108 stores insulin, and defines a chamber 224 for storing the fluid. With reference to FIG. 3A, the chamber 224 narrows or necks to the flange 180. The flange 180 is couplable to the first end 160 of the transfer device 106. The flange 180 defines a vial passageway 226. The vial passageway 226 provides a fluid flow path out of the chamber 224, and is closed with a septum 228. The septum 228 is disposed in the flange 180 and serves to prevent the ingress and egress of fluids out of the chamber 224 of the vial 108. The septum 228 is pierceable with the piercing member 168 to enable fluid flow out of the vial 108.

With reference to FIG. 4, the pressurizing device 110 is coupled to the second end 162 of the transfer device 106. As the pressurizing device 110 can comprise a suitable syringe, such as a 3.0 millimeter (mm) syringe, known to one skilled in the art, the pressurizing device 110 will not be discussed in great detail herein. Briefly, however, the pressure device includes a first end 230, a second end 232 and a fluid chamber 234 therebetween. The first end 230 can include a coupling flange 236 and a projection 238. The coupling flange 236 includes the at least one coupling feature 190, which engages the at least one coupling feature 188 of the second end 162 to couple the pressurizing device 110 to the transfer device 106. The projection 238 is received within the second branch 194 and includes a bore 239. The bore 239 is in fluid communication with the fluid chamber 234, and thus, creates a fluid flow path between the second branch 194 and the fluid chamber 234 of the pressurizing device 110.

The second end of the pressurizing device 110 includes a plunger 240. The plunger 240 is movable relative to the fluid chamber 234 to create a negative pressure (to draw fluid into the fluid chamber 234) and to create a positive pressure (to push fluid out of the fluid chamber 234). It should be noted that the use of a syringe is merely exemplary, as any device capable of creating a positive and a negative pressure can be employed with the system 100.

With reference to FIG. 3, in one example, in order to assemble the system 100, the delivery port 130 of the fluid reservoir 102 is inserted into the end 222 of the third branch 196 to couple the fluid reservoir 102 to the third branch 196 of the transfer device 106. With reference to FIG. 3A, the pressurizing device 110 is coupled to the second end 162 such that the at least one coupling feature 188 of the second end 162 of the transfer device 106 engages the at least one coupling feature 190 of the first end 230 of the pressurizing device 110. The vial 108 is coupled to the transfer device 106 such that the piercing tip 168a of the piercing member 168 pierces the septum 228 of the vial 108 and the ledge 178 cooperates with the edge 180a of the flange 180 of the vial 108 to retain the vial 108 at the first end 160. With the fluid reservoir 102, vial 108 and pressurizing device 110 coupled to the transfer device 106, the system 100 is fully assembled (FIG. 2). It should be noted that the assembly of the system 100 described herein is merely exemplary, as the system 100 can be assembled in any desired method.

With reference to FIGS. 3, 3A and 4, with the system 100 assembled, the user can move the plunger 240 (FIG. 4) away from the transfer device 106 (i.e. rearward) relative to the fluid chamber 234 of the pressurizing device 110 to create a negative pressure in the transfer device 106. The creation of the negative pressure by the pressurizing device 110 causes the second end 204 of the valve 200 to move from the first position to the second position, thereby opening a fluid flow path out of the vial 108, through the piercing member 168 and into the first branch 192 of the transfer device 106. The continued movement of the plunger 240 draws air from the transfer device 106 and the fluid through the filter 214, through the second passage 212 and the bore 239, and into the fluid chamber 234 of the pressurizing device 110. The fluid drawn through the filter 214 initially includes both air from the transfer device 106 and the fluid from the vial 108, which is insulin in this example.

With the fluid chamber 234 of the pressurizing device 110 filled with the air from the transfer device 106 and the fluid from the vial 108, the plunger 240 is moved relative to the fluid chamber 234 toward the transfer device 106 to create a positive pressure in the transfer device 106. The movement of the plunger 240 pushes the air and the fluid from the vial 108 toward the transfer device 106. As the filter 214 is a hydrophilic filter, the filter 214 allows only the fluid from the vial 108 into the transfer device 106, and prevents the air from entering the transfer device 106. Thus, any air in the system remains in the pressurizing device 110.

As the plunger 240 creates a positive pressure in the transfer device 106, the second end 204 of the valve 200 moves from the second position to the first position, thereby occluding the fluid flow path to/from the vial 108. Thus, the fluid that enters the transfer device 106 under positive pressure from the pressurizing device 110 is forced to flow through the third passage 220 into the delivery port 130 and the reservoir 128, thereby filling the reservoir 128. Thus, the system 100 enables the reservoir 128 to be filled with fluid from the vial 108, for example, insulin, with little to no air.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A transfer device for filling a fluid reservoir of a fluid infusion device with a fluid, the transfer device comprising:
a first end to couple to a source of the fluid;
a second end to couple to a pressurizing device; and
a body interconnecting the first end and the second end and having an end to couple to the fluid reservoir, the body having a first branch coupled to the first end, a second branch coupled to the second end and a third branch that defines the end of the body, the body defining at least one fluid flow path between the source of the fluid, the pressurizing device and the fluid reservoir to enable the filling of the fluid reservoir with the fluid and the body including a one-way duckbill valve that prevents the fluid from entering the source of the fluid located within the first branch and that opens upon the application of a negative pressure to the second end.

2. The transfer device of claim 1, wherein the first end includes at least one projection that extends upwardly from a base, and the at least one projection is to couple the source of the fluid to the transfer device.

3. The transfer device of claim 2, wherein the base includes a protrusion and the first end includes a piercing member coupled to the protrusion, and the piercing member establishes a fluid flow path from the source of the fluid into the transfer device.

4. The transfer device of claim 1, wherein the first branch defines a passage, the second branch defines a second passage and the third branch defines a third passage, with the passage, the second passage and the third passage defining the at least one fluid flow path between the source of the fluid, the pressurizing device and the fluid reservoir.

5. The transfer device of claim 4, wherein a filter is coupled to the second passage to restrict the flow of fluid into the second passage.

6. The transfer device of claim 5, wherein the filter is a hydrophilic filter and restricts the flow of air into the second passage.

7. A system for filling a fluid reservoir of a fluid infusion device with a fluid, comprising:
the fluid reservoir including a port for receipt of the fluid; and
a transfer device having a body with an end coupleable to the port of the fluid reservoir, a first end to couple to a source of the fluid and a second end to couple to a pressurizing device, the first end having a base to couple to the source of the fluid and a piercing member, the base includes a protrusion and the piercing member is coupled to the protrusion, the piercing member establishes a flow path from the source of the fluid into a first branch of the transfer device, and a one-way valve is coupled to an end of the piercing member that prevents the fluid from entering the source of the fluid, the one-way valve located within the first branch of the body, wherein the body defines at least one fluid flow path between the source of the fluid, the pressurizing device and the fluid reservoir to enable the filling of the fluid reservoir with the fluid.

8. The system of claim 7, wherein the first end includes two projections that each extend upwardly from the base, and the projections are spaced apart to couple the source of the fluid to the transfer device.

9. The system of claim 7, wherein the first branch is coupled to the first end, and the body further comprises a second branch coupled to the second end and a third branch that defines the end of the body.

10. The system of claim 9, wherein the first branch defines a passage, the second branch defines a second passage and the third branch defines a third passage, with the passage, the second passage and the third passage defining the at least one fluid flow path between the source of the fluid, the pressurizing device and the fluid reservoir.

11. The system of claim 10, wherein the one-way valve is located within the passage of the first branch.

12. The system of claim 9, wherein the first branch and the second branch are parallel to a longitudinal axis of the transfer device, and the third branch is transverse to the longitudinal axis of the transfer device.

13. The system of claim 10, wherein a filter is coupled to the second passage to restrict the flow of air into the transfer device.

14. A system for filling a fluid reservoir of a fluid infusion device with a fluid, comprising:

a source of pressure;

the fluid reservoir including a port for receipt of the fluid; and a transfer device including a body having a first branch, a second branch and a third branch, the first branch to couple to a source of the fluid, the second branch coupleable to the source of pressure and the third branch coupleable to the fluid reservoir, the first branch having a base to couple to the source of the fluid and a piercing member, the base includes a protrusion and the piercing member is coupled to the protrusion, the piercing member establishes a flow path from the source of the fluid into the transfer device, with a one-way valve that prevents the fluid from entering the source of the fluid disposed in the first branch and coupled to an end of the piercing member, the one-way valve responsive to the source of pressure to permit the fluid to flow into the body and the body defines at least one fluid flow path between the source of the fluid, the source of pressure and the fluid reservoir to enable the filling of the fluid reservoir with the fluid.

15. The system of claim 14, wherein the one-way valve opens upon the application of a negative pressure to the second branch of the body by the source of pressure.

16. The system of claim 14, wherein a hydrophilic filter is coupled to the second branch to restrict the flow of air into the body.

* * * * *